United States Patent [19]

Suzuki et al.

[11] Patent Number: 5,010,594
[45] Date of Patent: Apr. 30, 1991

[54] DAMPENING MASK FOR USE IN AIRCRAFT

[75] Inventors: Shigeaki Suzuki, Yokohama; Hideo Inoue, Tokyo, both of Japan

[73] Assignee: Japan Air Lines Co., Ltd., Tokyo, Japan

[21] Appl. No.: 371,971

[22] Filed: Jun. 27, 1989

[51] Int. Cl.$^5$ ............................................. A62B 18/02
[52] U.S. Cl. .................................... 2/206; 128/201.13; 128/206.12
[58] Field of Search .................................. 2/206, 6, 9; 128/201.13, 206.12, 206.16; 165/10

[56] References Cited

U.S. PATENT DOCUMENTS

| | | | |
|---|---|---|---|
| 2,348,108 | 5/1944 | Bulbulian | 128/201.13 |
| 3,814,094 | 6/1974 | De Angelis et al. | 128/201.13 |
| 3,835,853 | 9/1974 | Turner | 128/201.13 |
| 3,982,981 | 9/1976 | Takao et al. | 156/89 |
| 4,136,691 | 1/1979 | Ebeling et al. | 128/201.13 |
| 4,150,671 | 4/1979 | Tiger | 128/201.13 |
| 4,157,090 | 6/1979 | Phillips | 128/141 R |
| 4,196,728 | 4/1980 | Granite | 128/201.13 |
| 4,325,365 | 4/1982 | Barbuto | 128/201.13 |
| 4,327,717 | 5/1982 | Oetjen et al. | 128/201.13 |
| 4,458,679 | 6/1984 | Ward | 128/201.13 |
| 4,620,537 | 11/1986 | Brown | 128/201.13 |

FOREIGN PATENT DOCUMENTS

23279 of 1894 United Kingdom .

*Primary Examiner*—Peter Nerbun
*Assistant Examiner*—Michael A. Neas
*Attorney, Agent, or Firm*—Wenderoth, Lind & Ponack

[57] ABSTRACT

A dampening mask for use in aircraft, includes a mask body to be worn in a manner in which it is placed in front of the nose of the wearer to cover at least the nose, and forming a small space separated from the outside air in front of the nose; and a ventilation-passage member provided in a portion of the mask body which is, when the mask is worn, situated in front of the nose, the ventilation-passage member interconnecting the small space and the outside air in communication, the ventilation-passage member being a honeycomb structure made of a moisture absorbing material which has a function of absorbing and releasing moisture, the honeycomb structure having a large number of ventilation passages (tubular cavities) directed forward so as to form passages for air.

8 Claims, 5 Drawing Sheets

DAMPENING MASK FOR USE IN AIRCRAFT

BACKGROUND OF THE INVENTION

1. Field of the Invention

The present invention relates to dampening masks for use in aircraft, and more paticularly to dampening masks having a function or absorbing moisture contained in breath exhaled through a human nose or mouth and, during inhalation, dampening inhaled breath by giving off the previously absorbed moisture.

2. Description of the Related Art

It is generally known that the air within aircraft is very dry. This is because the outside air temperature at high altitudes at which the aircraft flies is very low, typically −40° C. to −70° C., and thus the outside air taken into the inner space of te aircraft is very dry. Generally, however, the aircraft is not provided with any dampening devices, because such devices will add to the weight of the aircraft and will further cause ill effects, such as condensed water on the cold inner walls of the aircraft or icing and water contamination. Excessively dried air in the aircraft is not preferable for the passengers and crew, and will actually cause several environmental problems particularly during a long flight of about two or more hours. For example, travelers will frequently feel sensations of stimulus, pain or displeasure in the mucous membranses of the nose and the mout when respiring such extremely dried air. Such problems which occur in connection with the respiration of extremely dry air in aircraft will sometimes cause significant pain or displeasure particularly during sleep unless the respired air is moderately humid, because the vital dampening function performed in the nose is weakened during sleep. This is pointed out in the SAE report AIR1609 (Apr. 30, 1982), United States Automobile Engineering Association, for example.

In view of the foregoing problems, it is desired to improve the environment for persons in aircraft. However, it is not practical to dampen the air within the aircraft to solve the above problems. So, it is difficult to improve the environment in the aircraft and any simple and effective means for doing so has of yet not been proposed.

The inventors studied and developed various subjects in attempts to achieve advances in the above-described problems, and eventually came to note the following facts:

Human respiration is a series of repeated actions of exhaling and inhaling. Generally, the relative humidity of exhaled breath is almost 100%. Therefore, when respiration is performed in extremly dry air such as that in aircraft, the moisture contained in the exhaled breath is dispersed in the air in the aircraft while extremely dry air is inhaled through the nose or mouth. The continuation of respiration in such an environment causes the previously mentioned significant pair or displeasure.

In view of the foregoing, the inventors thought that if there is some means which would allow man to temporarily retain moisture contained in exhaled breath without dispersing such moisture into the air and would further allow man to inhale such retained moisture together with air, then such means would be an effective measure to solve the above-mentioned problems.

Japanese Patent Publication No. 20557/1971 discloses an idea relying on the nature of inhaled and exhaled breath and proposes a mask of the type having fibers wound on heat exchangers made of aluminum, for example, the fibers being capable of absorbing moisture well, for the purposes of warming cold inhaled breath of imparting the temporarily absorbed moisture to the inhaled breath. The proposed mask, however, works depending on substantial temperature differences between the exhaled breath (at body temperature) and the outside air temperature, and cannot function well in an environment such as that in aircraft where the air is conditioned to a suitable temperature (usually, 23° to 26° C.).

SUMMARY OF THE INVENTION

The present invention has been made in view of the foregoing problems, and its one object which is to provide a mask for use in connection with the extremely dried environment in aircraft, said mask having a moisture absorbing member made of paper, for example, which absorbs moisture contained in exhaled breath while allowing the absorbed moisture to be released into inhaled extremely dry air, whereby the extremely dry air can be efficiently dampened to within a range of relatively humidity of 30 to 85 RH %, preferably 40 to 70 RH %. Within such a range, displeasure will not normally be felt.

Generally, the purpose of masks for use in aircraft, unlike various special emergency masks to be used in case of a disaster, such as a fire, is to suitably dampen air in aircraft in which the environment is not so different from usually experienced environments except in that it is extremely dry. Aircraft masks are frequently requested to be disposable from the point of view of hygiene. Thus, another object of the present invention is to provide a dampening masks which has a simple structure and which can be provided at low costs.

In order to achieve the above objects, the dampening mask according to the present invention comprises: a mask body to be worn in a manner in which it is placed in front of the nose and lips to cover them, and forming a small space separated from the outside air in front of the nose and lips; and a ventilation-passage member provided in a portion of the mask body which is, when the mask is worn, situated in front of the nose and lips, said ventilation-passage member placing said small space and the outside in communication, said ventilation-passage member being a honeycomb structure made of a moisture absorbing material such as paper, for example, which has a function of absorbing and releasing moisture, said honeycomb structure having a large number of tubular cavities directed forward so as to form passages for air. It is desirable for said ventilation-passage member to have a total ventilation resistance lower than 5 mb, preferably lower than 2 mb. A total ventilation resistance of a value within such a range would not normally offer a significant resistance to respiration.

The moisture absorbing material for forming the honeycomb structure may be paper such as, for example, Japanese paper manufactured from bast fibers. The invention is not limited to such paper, but can also employ any other material as long as it has a function of absorbing and releasing moisture so that the air respired through such material can be maintained at a relative humidity within a range of 30 to 80 RH %, preferably 40 to 70 RH %, whereby displeasure durins respiration would not be felt. For example, a composite material comprising a sponge-like sheet having paper laminated thereon may be used.

Japanese paper, used in Japan since old times, is particularly preferably as the said moisture absorbing material. Such paper can take the form of a sheet manufactured by hand or on a machine using bast fibers as the raw material without using any binder, the bast fibers being non-wood fibers represented by paper mulberry, paper bush and Gampi. Japanese paper manufactured in the manner described immediately above has a suitable function of quickly absorbing moisture from air having a high relative humidity and releasing moisture into air at relative humidity of near zero.

The reason why moisture absorbing paper is used in accordance with the present invention is that, as compared with other absorbing materials such as woven fabric, such paper has a particularly suitable function of absorbing moisture from exhaled breath at about 100 RH % and releasing moisture into inhaled breath at about 0 RH %. Generally, the moisture content of paper, with respect to it being a moisture absorbing material, is expressed in connection with the relative humidity (RH %) of the surrounding gas as follows:

$$\text{coefficient of moisture absorption} = \frac{(W - W_o)}{W_o} \times 100$$

where " represents the weight of a quantity of paper at a constant humidity, and "$W_o$" represents the weight of the same quantity of the paper in a reference dried state.

Therefore, in the environment in which the moisture absorbing mask according to the present invention is to be used, i.e. in aircraft in which air is extremely dry (at a relative humidity of about 0 RH %), the objects of the present invention can be achieved by selecting suitable types of paper having moisture absorbing characteristics which allow only a small fraction of the moisture contained in exhaled breath (at about 100 RH %) to be released into the extremely dried ambient air and which thus allow moisture to be recycled from exhaled breath, and by ensuring that a sufficient area of such paper will contact with respired air in view of the characteristic (particularly the coefficient of moisture absorption) of such paper and the ventilation resistance offered thereby.

The coefficient of moisture absorption varies with the type of paper. Generally, the so-called Japanese paper manufactured using bast fibers has a higher coefficient of moisture absorption than the so-called pulp paper manufactured using wood fibers.

The reason why Japanese paper, a sheet-shaped material made of bast fibers, is preferred in accordance with the present invention is that it exhibits a hysteresis in which it achieves an equilibrium state with the ambient air in terms of relative humidity in a relatively short time while the time required for the absorption and releasing of moisture is not too long or too short relative to, and almost equals, the duration inhalation and exhalation when normal respiration is performed, whereby preferable moisture absorbing and releasing characteristics suitable for respiration in the environment in aircraft can be achieved.

The present invention provides that the total surface area of said honeycomb structure should be 450 $cm^2$ or larger so that a necessary and sufficient surface of said paper can be ensured for absorbed or released moisture equivalent to the typical volume of breath inhaled or exhaled during normal respiration. If the area is smaller than 450 $cm^2$, the quantity of moisture released into inhaled breath is insufficient because a sufficient quantity of moisture cannot be absorbed from the exhaled breath, with the result that a person wearing it will inhale insufficiently dampened air and will eventually feel a sensation associated with the inhalation of dry air. Nevertheless, the humidity adjusting function of the mask will not be much improved by increasing the total surface area to more than 450 $cm^2$, because the absolute quantity of moisture contained in exhaled breath is limited and it is desirable that the humidity of inhaled breath should be maintained within a range of 40 to 60 RH % which is considered a normally comfortable humidity range. Therefore, the total surface area should typically be 1000 to 3000 $cm^2$, preferably 1500 to 2500 $cm^2$.

The tubular cavities or ventilation passages formed in the honeycomb structure of the ventilation-passage member made from a moisture absorbing material will offer a ventilation resistance (resistance to respiration) which is, when excessively large, an obstacle to respiration that would eventually cause the wearer to feel choky. In view of this, the honeycomb structure should be arranged such that the total ventilation resistance is 5 mb or less, preferably 2 mb or less.

Figure 9A:
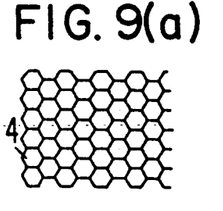
FIGS. 9(a)–9(n) show examples of the form of the honeycomb core.
Figure 9B:
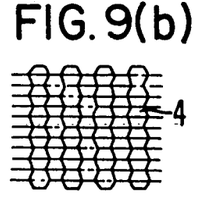
Figure 9C:
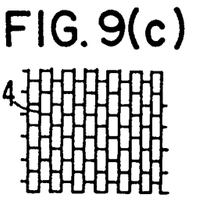
Figure 9D:
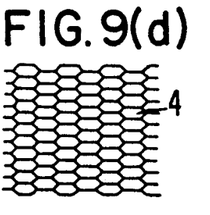
Figure 9E:
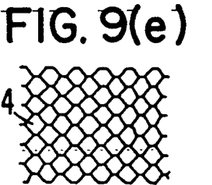
Figure 9F:
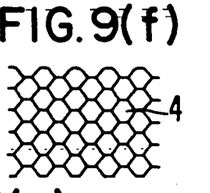
Figure 9G:
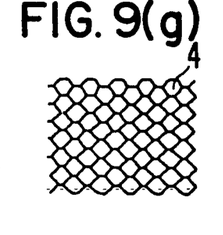
Figure 9H:
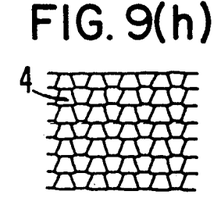
Figure 9I:
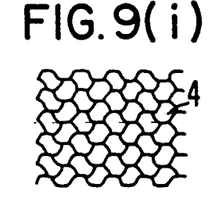
Figure 9J:
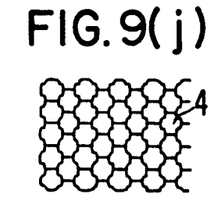
Figure 9K:
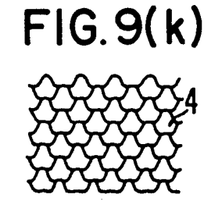
Figure 9L:
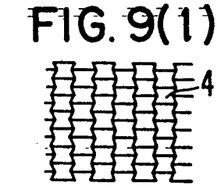
Figure 9M:
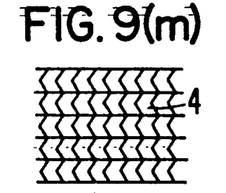
Figure 9N:
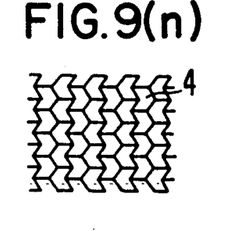

The honeycomb structure according to the present invention has a total surface area facing the ventilation passages which is within the above-described range and offers a ventilation resistance within the range described above, and may take the form of any of the types shown in FIGS. 9(a)–(n) and may also be one comprising a plurality of tubular members bound together.

BRIEF DESCRIPTION OF THE DRAWINGS

FIG. 3 (a) shows a form of a honeycomb core;

DETAILED DESCRIPTION OF THE PREFERRED EMBODIMENTS

The present invention will now be described, by way of example, with reference to the accompanying drawings.

Figures 1A, 1B:
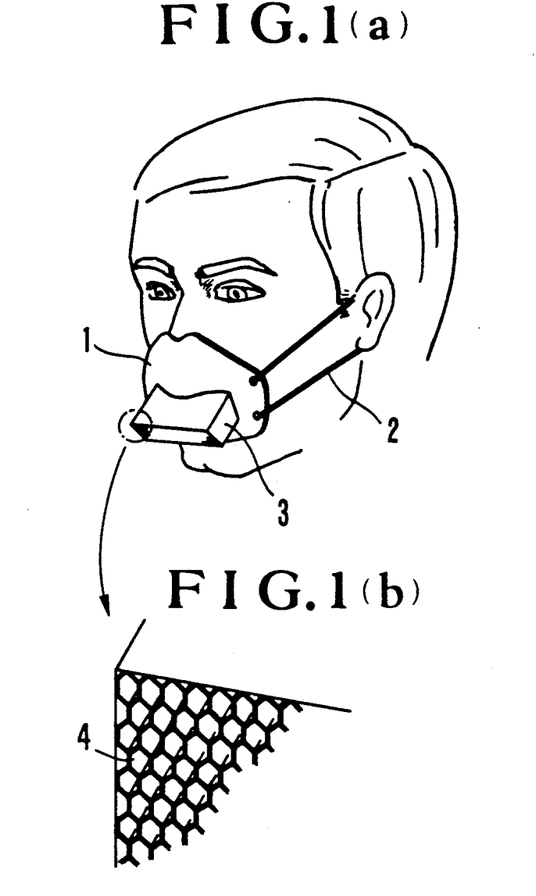
FIG. 1(a) is a schematic of an embodiment of a dampening mask according to the present invention, as worn by a person.
FIG. 1(b) is an enlarged view of part of the honeycomb structure.
Figure 2:
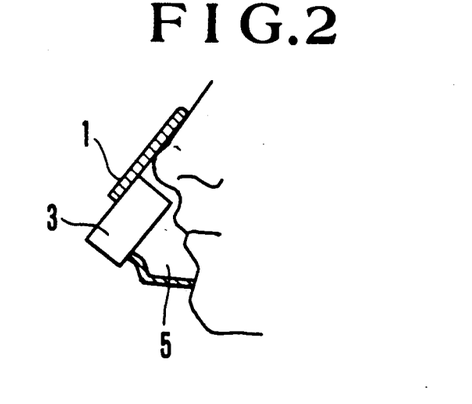
FIG. 2 is a partially cutaway side view of the invention as shown in FIG. 1.

Now referring to the drawings, FIG. 1 and FIG. 2 show an embodiment of the moisture absorbing mask according to the present invention, worn by a person. In these figures, reference numeral 1 designates a moisture absorbing mask body, which is adopted to cover the nose and lips of the face and forms a small space 5 separated from outside air. If this small space is too large, a large proportion of exhaled breath containing a high density of carbon dioxide will be subsequently inhaled, with the result that the wearer will feel choky. Therefore, the space should be as small as possible.

Application bands 2 are attached to both sides of the moisture absorbing mask body 1. Said small space has a volume of 20 cm$^3$.

The sum of the volumes of said small space and the honeycomb structure is considered to be the dead space of the mask, where a portion of exhaled breath can remain and be subsequently inhaled. Therefore, this space should be as small as possible, and should be of 180 cm$^3$ or smaller, preferably 50 cm$^3$ or smaller.

The moisture absorbing mask body 1 has provided on its front face a honeycomb structure 3 formed of Japanese paper manufactured from Gampi fibers, a large number of tubular cavities of the honeycomb forming ventilation passage (or tubular cavities) 4 between the space 5 and the outside air. In this example, the ventilation passages 4 of the honeycomb structure 3 are formed to extend in the direction in which air is inhaled or exhaled through the nose in order for the ventilation resistance to be as small as possible. As can be understood from FIG. 1(b), the honeycomb structure 3 is generally a rectangular parallelepiped with said ventilation passage 4 open at the two opposite ends (front end facing outward and rear end facing said small space) of the parallelepiped.

Figure 3A:
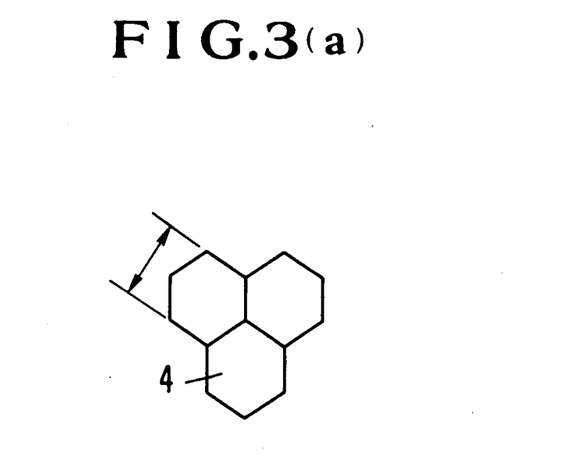

As already mentioned, the honeycomb structure 3 is manufactured using Japanese paper as a material, the Japanese paper being machine-manufactured, using Gampi fibers as a material, into sheets each having a thickness of 0.05 mm. The sheets defining a large number of core cells each having a dimension of 0.3 cm as shown in FIG. 3(a), are adhered to one another by a binder (emulsion of vinyl acetate soluble in water) so as to form a rectangular parallelepiped honeycomb that is 3 cm thick, 2 cm high, and 4 cm long.

Figure 3B:
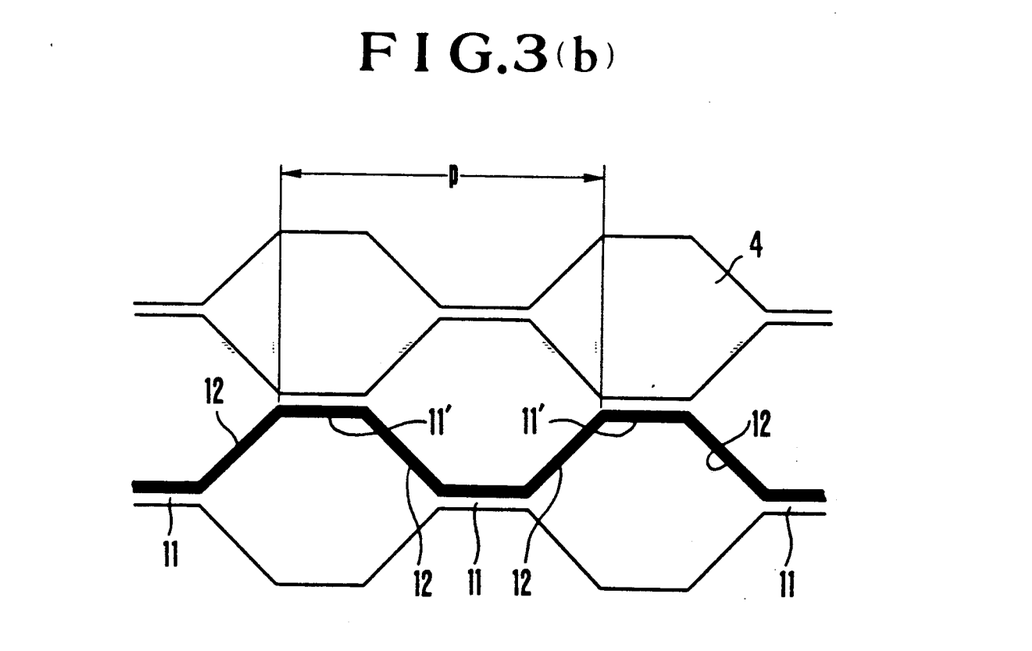
FIG. 3(b) is a schematic diagram illustrating the actual structure of the honeycomb.

The honeycomb structure is made by a process in which an adhesive binder is intermittently applied to portions of each paper sheet and the paper sheets are adhered to one another with the binder-covered portions of adjacent paper sheets staggered, as shown in FIG. 3(b). About seventy paper sheets were used. Thus, in the honeycomb structure shown in FIG. 3(b), the utilization factor of one face of a paper sheet shown by a thick solid line is 6/8 per pitch shown by reference numerals 11, 12, 11' and 12 in the figure (one face is counted as 1).

In this example of the honeycomb structure 3, the total surface area facing the ventilation passages 4 was 1800 cm$^2$, and offered a ventilation resistance of 2 mb or less.

The above-described moisture absorbing mask was tested with respect to the absorption and release of moisture in aircraft in a manner as follows:

EXAMPLE 1

(Testing Conditions)

Air in aircraft . . . relative humidity: about 0.7 RH % . . . temperature: about 28° C.

Figure 4:
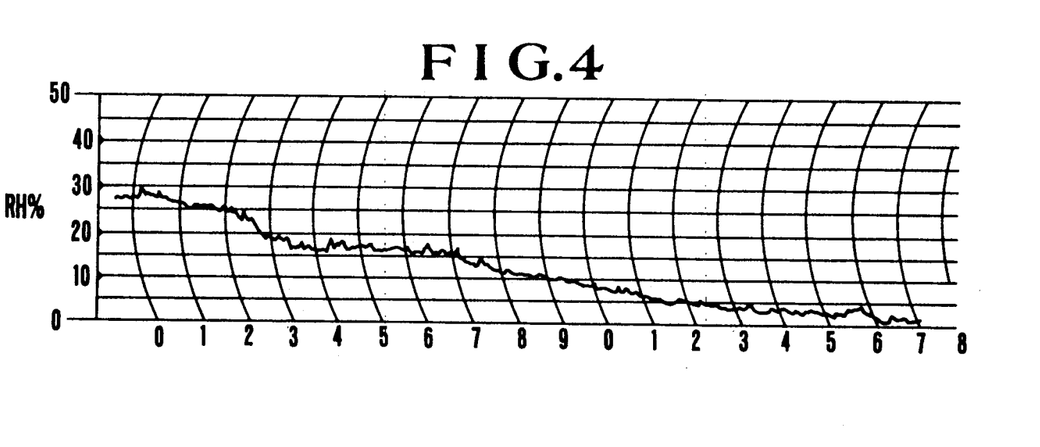
FIG. 4 is a graph showing the change in relative humidity of air in aircraft.

The air in the aircraft reached a state in which the relative humidity was 0.7 RH % in about 19 min. after takeoff, and was maintained in such state during flight at high altitudes. See FIG. 4.

(Measurement of Absorption and Release of Moisture by The Honeycomb)

Figure 5:
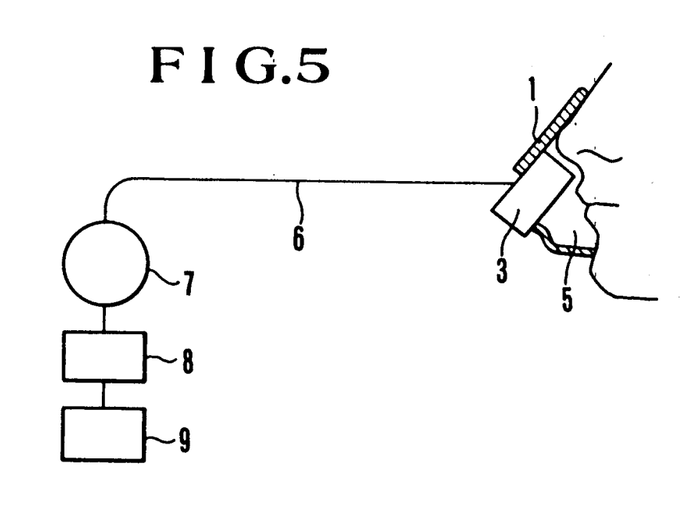
FIG. 5 is a schematic diagram of a device for measuring the relative humidity in the mask.

Measurements of the absorption and release of moisture was taken in a manner shown in FIG. 5 by introducing air in the mask into a measuring cavity 7 through a duct 6, the humidity in the cavity being measured by a humidity measuring apparatus 8 available from VAISALA (thermometer and hygrometer HMI32) which measure humidity relying on capacitance changes. The measurements were recorded by a pen recorder 9 (type 8202 recorder manufactured by the Hioki Electric Works, Ltd.). Further, the difference between the air pressure within the mask body and the atmospheric pressure was measured by a not-shown micromanometer (i/a 7321 manufactured by KRONE, U.S.A.).

Figure 6:
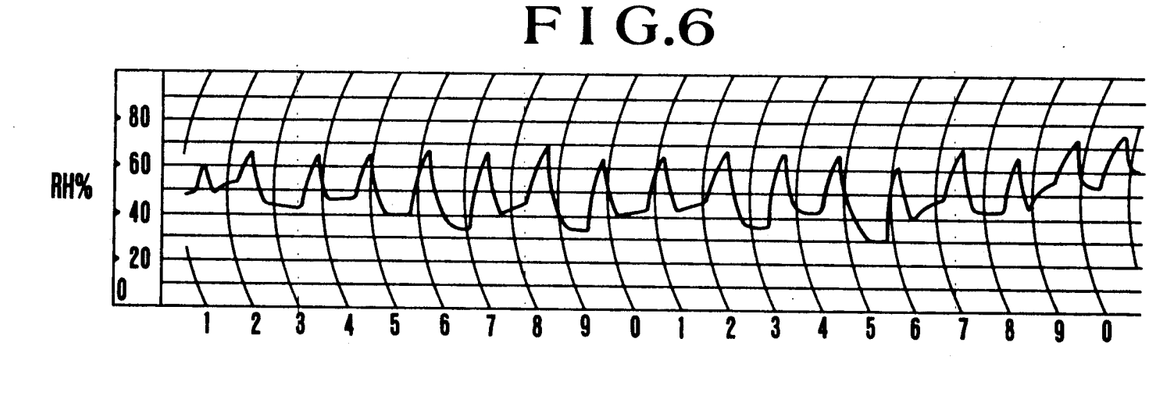
FIG. 6 is a graph showing the change in relative humidity of inhaled air when the mask of FIG. 1 is worn.

Measurements thus taken are shown in FIG. 6.

As can be understood from FIG. 6, changes in relative humidity during breathing cycles in which breath was inhaled intermittently drawn were measured. The portion of the curve between adjacent apexes corresponds to one complete cycle of respiration, while the portion between one apex and an adjacent valley shows the variation of humidity of inhaled breath. The portion between each valley and the following apex corresponds to exhaled breath, which was not recorded on the recording sheet, since it is known that the humidity of exhaled breath is almost 100 RH %. In the moisture absorbing mask of the present invention, the relative humidity of inhaled breath reached 60 RH % or higher at an initial stage of an inhalation and then dropped to about 40 RH % toward the end of the inhalation.

Comparison

Figure 7:
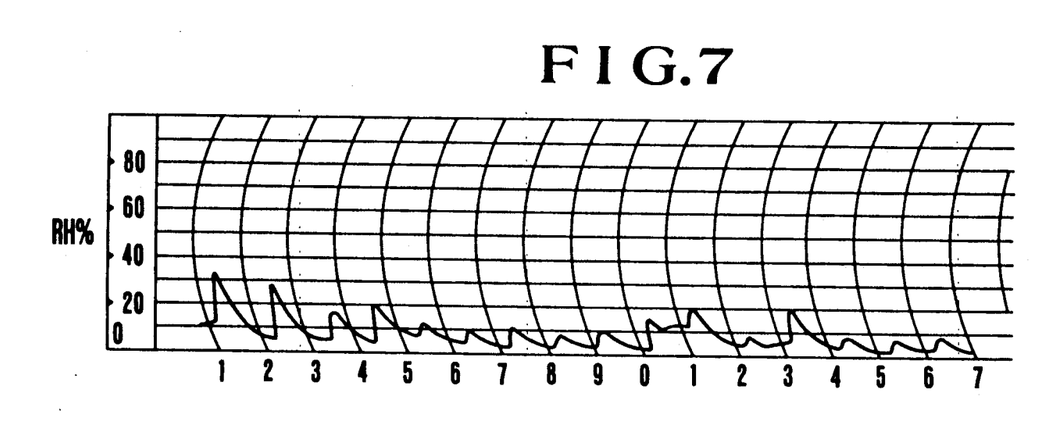
FIG. 7 is a graph showing the change in relative humidity of inhaled air when a comparative example of a mask is worn.

For comparison with the above-described Example 1, a mask (not shown) was made which did not have the honeycomb structure 3 but merely employed an opening in the location where the honeycomb is provided in the above-mentioned example of the invention. Humidity changes of air through such an opening were measured. Measuresments were taken under the same testing conditions and by the same process as in Example 1.

Results are shown in FIG. 7. As understood from this figure, the relative humidity of inhaled breath flowing through the mask lacking the honeycomb structure changed between 5 and    RH%. Thus, the advantageous effects of the present invention are clear.

EXAMPLES 2 AND 3

A mask having a different honeycomb structure listed in the following table was tested. Such a honeycomb structure was made using the same sructural material and process as those used in Example 1. Measurements of the relative humidity taken at initial and end stages of inhalation are shown in Table 1 below.

TABLE 1

|  | Example 2 | Example 3 |
|---|---|---|
| Measuring phase |  |  |
| Outer dimensions of honeycomb structure (cm) | 1.5 W × 4.5 H × 1.5 L | 2 W × 5 H × 7 L |
| Number of paper sheets constituting the honeycomb (pieces) | 30 | 40 |
| Total surface area | 456 | 4200 |

TABLE 1-continued

|  | Example 2 | Example 3 |
|---|---|---|
| (cm$^2$) | | |
| Humidity in mask at an initial phase of inhaling action (RH %) | 50 | 83 |
| Humidity in mask at an end phase of inhaling action (RH %) | 23 | 80 |

EXAMPLES 4 TO 9

Another mask made using paper manufactured from Gampi fibers, and having a thickness of 0.05 mm, was tested under the same conditions as was Example 1 except for:

| width: | 3.5 cm |
|---|---|
| height: | 2 cm |
| length: | 2 cm and 4 cm |
| total surface area: | 735 cm$^2$ |
|  | 1470 cm$^2$ |

The results are shown in Table 2 below.

TABLE 2

| | | Room temperature 25° C., 15% RH | | | | | |
|---|---|---|---|---|---|---|---|
| | | Form of core | | | | | |
| | | | Core length 2.0 cm | | | Core length 4.0 cm | |
| Measured items | | Without core mounted | Rectangular parallele-piped | Divergence (central angle of sector, 50°) | Divergence (central angle of sector, 80°) | Rectangular parallele-piped | Divergence (central angle of sector, 40°) | Divergence (central angle of sector, 90°) |
| Inhaled air humidity (% RH) | Beginning of inhaling | 30 | 70 | 70 | 60 | 80 | 75 | 75 |
| | End of inhaling | 15 | 40 | 40 | 30 | 50 | 45 | 30 |
| Respiration resistance | During exhaling | 0 | 0.5 mm H$_2$O (0.05 mb) | — | — | 0.5 mm H$_2$O (0.05 mb) | — | — |
| | During inhaling | 0 | same as above | — | — | same as above | — | — |

Respiration resistances are peak values.

The results showed that the damping mask according to the present invention can exhibit an excellent performance in the extremely dry environments in aircraft.

Figure 8:
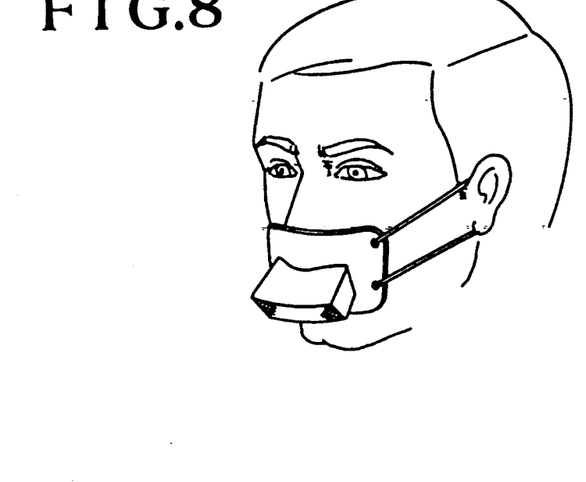
FIG. 8 is a schematic of another embodiment of the moisture absorbing mask.

Naturally, the present invention is not limited to the above-described particular embodiments. For example, the honeycomb structure can have a fan-like shape diverging at a front end therefore, as shown in FIG. 8, can have a slightly converging front end. Masks having either of such honeycomb structures, as compared with masks having a rectangular parallelepiped honeycomb structure, offer lower ventilation resistance, since the air flow through each core created by respiration is similar to the air flow created by respiration under natural conditions. And, moreover, such mask structures are suitable for facilitating miniaturization of the honeycomb structure since exhaled breath will equally flow through the cores and thus good absorption and release of moisture can be achieved throughout the structure.

As described previously, the damping mask for use in aircraft according to the present invention has a member for absorbing moisture from exhaled breath while releasing the absorbed moisture into inhaled breath, thereby efficiently dampening the dried inhaled breath, whereby the respiratory organs can be protected from excessive drying effects which would otherwise be experienced due to the extremely dry air in aircraft.

Therefore, the mask according to th present invention is advantageous from the point of view of health of the crew and passengers in aircraft, or from the point of view of maintaining a good environment in aircraft.

What is claimed is:

1. A dampening mask for dampening dry air of an environment to be respired by a wearer of the mask, said mask comprising:

a mask body of a size adapted to fit over at least the nose of a wearer and of a shape adapted to form a small space therein in front of the nose of a wearer that is separated by the mask body from the environment outside of the mask body; and a ventilation-passage member extending through said mask body from a location in front of the nose of a wearer when the mask body is fitted thereover, said ventilation-passage member comrpising a honeycomb structure of moisture absorbing material defining a plurality of tubular cavities through which air can pass between said space and the environment outside of the mask body when the mask body is fitted over at least the nose of the wearer, said moisture absorbing material being Japanese paper comprising bast fibers, and said Japanese paper capable of absorbing moisture in dampened air passing through said cavities and capable of releasing moisture absorbed thereby to dry air passing through said cavities, whereby when the mask is worn in an enviornment of dry air, respiration through said ventilation-passage member causes moisture in air being exhaled to be absorbed by said Japanese paper and causes moisture absorbed by said Japanese paper to be released to air being inhaled.

2. A dampening mask as claimed in claim 1, wherein said bast fibers are fifers selected from the group consisting of paper mulberry, paper bush and Gampi.

3. A dampening mask as claimed in claim 1, wherein a total resistance offered by said honeycomb structure against a passage of air respired therethrough is at most 5 mb.

4. A dampening mask as claimed in claim 2, wherein a total resistance offered by said honeycomb structure against a passage of air respired therethrough is at most 5 mb.

5. A dampening mask as claimed in claim 1, wherein a total surface area of portions of said honeycomb structure confronting said tubular cavities is at least 450 cm$^2$.

6. A dampening mask as claimed in claim 2, wherein a total surface area of portions of said honeycomb structure confronting said tubular cavities is at least 450 cm$^2$.

7. A dampening mask for dampening dry air of an environment to be respired by a wearer of the mask, said mask comprising:
- a mask body of a size adapted to fit over at least the nose of a wearer and of a shape adapted to form a small space therein in front of the nose of a wearer that is separated by the mask body from the environment outside of the mask body; and
- a ventilation-passage member extending through said mask body from a location in front of the nose of a wearer when the mask body is fitted thereover,
- said ventilation-passage member comprising a honeycomb structure of moisture absorbing material defining a plurality of tubular cavities through which air can pass between said space and the environment outside of the mask body when the mask body is fitted over at least the nose of the wearer, a total resistance offered by said honeycomb structure against a passage of air respired therethrough being at most 5 mb,
- said moisture absorbing material capable of absorbing moisture in dampened air passing through said cavities and capable of releasing moisture absorbed thereby to dry air passing through said cavities, whereby when the mask is worn in an environment of dry air, respiration through said ventilation-passage member causes moisture in air being exhaled to be absorbed by said material and causes moisture absorbed by said material to be released to air being inhaled.

8. A dampening mask for dampening dry air of an environment to be respired by a wearer of the mask, said mask comprising:
- a mask body of a size adapted to fit over at least the nose of a wearer and of a shape adapted to form a small space therein in front of the nose of a wearer that is separated by the mask body from the environment outside of the mask body; and
- a ventilation-passage member extending through said mask body from a location in front of the nose of a wearer when the mask body is fitted thereover,
- said ventilation-passage member comprising a honeycomb structure of moisture absorbing material defining a plurality of tubular cavities through which air can pass between said space and the environment outside of the mask body when the mask body is fitted over at least the nose of the wearer, a total surface area of portions of said honeycomb structure confronting said tubular cavities being at least 450 cm$^2$,
- said moisture absorbing material capable of absorbing moisture in dampened air passing through said cavities and capable of releasing moisture absorbed thereby to dry air passing through said cavities, whereby when the mask is worn in an environment of dry air, respiration through said ventilation-passage member causes moisture in air being exhaled to be absorbed by said material and causes moisture absorbed by said material to be released to air being inhaled.

* * * * *